United States Patent [19]

Felthauser et al.

[11] Patent Number: 5,420,786
[45] Date of Patent: May 30, 1995

[54] METHOD OF ESTIMATING PRODUCT DISTRIBUTION

[75] Inventors: Mark A. Felthauser, Merion; Preston L. McHenry, Blue Bell; Harold J. Petrimoulx, Phoenixville; Jeffrey B. Schott, Chalfont, all of Pa.

[73] Assignee: IMS America, Ltd., Plymouth Meeting, Pa.

[21] Appl. No.: 42,518

[22] Filed: Apr. 5, 1993

[51] Int. Cl.⁶ .............................................. G06F 15/21
[52] U.S. Cl. ..................................... 364/401; 364/402
[58] Field of Search ............... 364/400, 401, 402, 408, 364/578; 455/2; 358/84

[56] References Cited

U.S. PATENT DOCUMENTS

| | | | |
|---|---|---|---|
| 4,926,394 | 5/1990 | Doyen | 367/73 |
| 4,972,504 | 11/1990 | Daniel, Jr. et al. | 455/2 |
| 4,975,843 | 12/1990 | Brunnett et al. | 364/413.14 |
| 4,995,011 | 2/1991 | Spiesberger | 367/127 |
| 5,063,519 | 11/1991 | Zison | 364/510 |
| 5,198,979 | 3/1993 | Moorhead et al. | 364/421 |

OTHER PUBLICATIONS

*Data SOurces*, Software 1st Edition–vol. 2, 1989, Computer Associates Int., Inc., pp. J-215 to J-224, pp. J-653 to J-659, pp. J-637 to J-638, pp. J-493 to J-496.
DataPro Software Directory, 1991, McGraw-Hill, Inc., pp. D85-200-001 to D85-200-013.
"Small-Area Estimation of Economic Statistics" by Cary T. Isaki; Journal of Business & Economic Statistics, Oct. 1990, vol. 8, No. 4; pp. 435–441.

*Primary Examiner*—David M. Huntley
*Attorney, Agent, or Firm*—Fitzpatrick, Cella, Harper & Scinto

[57] ABSTRACT

Sales activity of a product at sales outlets including sales outlets at which sales activity data is sampled and unsampled sales outlets is estimated by determining the distances between each of the sampled sales outlets and each of the unsampled sales outlets and correlating sales activity data from the sampled sales outlets according to the determined distances. The sales activity volume of the product at the plurality of sampled outlets and the estimated sales activity volume of the product at the unsampled outlets are combined to obtain an estimate of sales activity for all the sales outlets. Sales activity of products prescribed by a physician at both the sampled and unsampled outlets can be estimated by correlating sales activity data for the prescribing physician at the sampled outlets according to the distances between the sampled outlets and the unsampled outlets.

15 Claims, 8 Drawing Sheets

METHOD OF ESTIMATING PRODUCT DISTRIBUTION

BACKGROUND OF THE INVENTION

1. Field of the Invention

The invention relates to marketing of products and, more particularly, to arrangements for estimating product distribution and sales.

2. Background of the Invention

Manufacturers and distributors of retail products generally monitor product sales in order to maintain proper inventory and to direct marketing efforts. Monitoring may be done by sampling sales at retail outlets and transferring sales data to a central point for evaluation. Retail outlets usually cooperate in providing sales data but a significant number of retail outlets are not able to or do not elect to have sales data sampled in a form needed for analysis. As a result, it is necessary to estimate product sales of unsampled and poorly sampled individual outlets to provide marketing information.

In some industries, distribution of certain products is controlled so that additional data relating to the control of such products is needed for marketing purposes. In the pharmaceutical industry, for example, many products are sold by prescription and such sales are controlled by prescribing physicians. As a result, it is desirable to determine the number of prescriptions written by a physician so that marketing efforts may be directed at the prescribing physicians.

Estimates of business sales in small areas such as counties of a state have been made on the basis of known data for the state under the assumption that the relationships for the state also hold for the county. The article "Small-Area Estimation of Economic Statistics" by Cary T. Isaki, Journal of Business and Economic Statistics, Vol. D, No. 4, Oct. 1990, pages 435-441 describes a ratio correlation (multiple regression) approach for estimating retail sales for small areas (counties) using county-to-state shares of retail sales from two successive economic censuses. While these methods provide estimates of retail sales over a relatively small county area from publicly available data, they are not adapted to estimate retail sales of individual outlets where individual outlet characteristics differ widely. As a result, the estimates for individual outlets based on wide area data are biased and may not reflect actual sales of an individual outlet.

Estimation of physician prescribing activity has been attempted by marketing research practitioners based on ratio estimators and inflation factor estimators as commonly described in such texts as "Sampling Techniques" by W. G. Cochran, John Wiley, New York 1977. These methods attempt to estimate the activity in a pre-established geographic area of known dimensions by scaling up a sample of activity within the area in proportion to the level of a known auxiliary variable (i.e., ratio estimate) or in proportion to the level of sample coverage (via an inflation factor) for the entire area. Typical geographic areas encompass a plurality of outlets and prescribers. Such geographic-based methods do not yield estimates of each individual prescriber's activity within each individual outlet but only produce a measure of the total activity for the geography. If prescriber level estimates are desired, these methods must assume that the proportion of the total activity that is captured in the sample data (i.e., the captured proportion) of each prescriber is the same. If outlet estimates are desired, it must then be assumed that each unsampled outlet is accurately represented by the average of the sampled outlets in the geography. With these assumptions, all sample data within a stratum receive the same "scale-up" factor. These assumptions, however, are known to be false and result in biased estimates at the activity source level.

It is well known in the fields of resource exploration and mining to estimate data at locations which are not sampled and for which data is unavailable using data acquired at sampled locations by spatial correlation according to known physical principles. Stanley W. Zison U.S. Pat. No. 5,063,519 issued Nov. 5, 1991, for example, describes a method for estimating landfill gas production by measuring gas pressure in a soil cover at randomly selected locations in the landfill. A contour estimation of flow is generated and a prediction of the continuous spatial distribution of the landfill gas is produced.

John L. Spiesberger U.S. Pat. No. 4,995,011 issued Feb. 19, 1991 describes an acoustic mapping system in which the positions of acoustic transmitters is determined by processing data from five or more receivers distributed in a marine or terrestrial environment. The processing includes cross correlation of the receiver data and provides displays of computer generated maps.

Philip M. Doyen U.S. Pat. No. 4,926,394 issued May 15, 1990 discloses a Monte Carlo method for estimating lithography from seismic data in which discrete geological measurements of rock properties are combined with continuous measurements of seismic attributes. The combined measurements are converted into a display of the best estimate of subsurface rock classes.

The aforementioned patents are directed to spatially continuous processes in which estimation is done either by interpolating continuous spatial processes from data at known locations or by Monte Carlo simulations using the known data to determine an optimized estimate. In each process, reliance is placed on the laws of the underlying continuous physical process. It would be desirable to use spatial correlation to provide estimates of retail sales. Sales outlets such as pharmacies, however, do not form a group to which a common physical process applies but each outlet is a separate discrete entity with its own characteristics. Consequently, there is no underlying continuous physical process on which to base such correlation as in the aforementioned patents.

BRIEF SUMMARY OF THE INVENTION

The invention is directed to estimating sales activity of a product by determining the distances between first sales outlets from which sales activity data are obtained and other sales outlets and correlating the sales activity data of the first sales outlets according to the determined distances between the first and the other sales outlets.

In contrast to priorly known arrangements, the invention provides unbiased estimates of activity that are produced at the actual activity sources (i.e., each outlet and each prescriber at an outlet) and obviates the need for a predefined geographic area before estimates can be constructed. According to the invention, nearest neighboring outlet activity sources within spatial proximity of each known but unsampled outlet are identified and the estimate of unsampled outlets is assembled by processing information on the discrete spatial correlation pattern among neighboring activity sources. The spatial correlation process between outlets is represented by the distribution pattern of each prescriber's prescription activity among a local neighborhood of outlets (sampled or unsampled). In practice, activity estimates may be made for greater than 20,000 unsampled outlet locations and greater than 600,000 activity sources (e.g., prescribing physicians) using large quantities of sampled data (e.g., $2 \times 10^9$ sample records).

According to one aspect of the invention, a distance between one sales outlet at which sales activity is not sampled and each of a plurality of sales outlets at which sales activity is sampled is determined. A group of the sampled sales outlets in a neighborhood of the one unsampled sales outlet is selected and sales activity data of the product at the selected sales outlet are combined according to the distances between the one unsampled sales outlet and the selected sales outlets to form an estimate of the sales at the unsampled sales outlet.

According to another aspect of the invention, the distances between the selected sampled sales outlets and the unsampled sales outlet are combined with parameters characterizing each sales outlet to form a signal representing an estimate of sales of the product at the unsampled sales outlet.

According to yet another aspect of the invention, product sales activity in an area including both sampled sales outlets and unsampled sales outlets are estimated by generating signals representative of the distances among the sales outlets, generating a signal representative of the type (e.g., size or sales volume) of each sales outlet, selecting a group of sampled sales outlets for each unsampled sales outlet, forming an estimate of the sales activity of each unsampled sales outlet according to the distances between the unsampled sales outlet and the associated selected sales outlet and the type representative signals for the unsampled and associated selected sampled sales outlets, and combining the sales activity data from the sampled sales outlets with the estimates of sales activity of the unsampled sales outlets.

According to yet another aspect of the invention, the prescription sales for a prescribing physician at a first prescription sales location in an area is estimated by correlating the prescription sales for the prescribing physician obtained from other prescription sales locations according to the distances between the first prescription sales location and selected ones of the other prescription sales locations.

According to yet another aspect of the invention, the prescription sales activity for a prescribing physician in an area including sampled prescription sales outlets and unsampled prescription sales outlets are estimated by generating signals representing distances among the prescription sales outlets, generating signals representing the size or total volume of prescription sales at each prescription sales outlet, selecting a group of sampled outlets closest to each unsampled outlet and forming an estimate of prescription sales for the prescribing physician at each unsampled outlet according to the distances between the unsampled outlet and the selected sampled outlets and the size or total volume of the outlets. A signal representative of the prescription sales for the prescribing physician is produced according to the sales for the prescribing physician at the sampled outlets and the estimates of the sales for the prescribing physician at the unsampled outlets.

According to yet another aspect of the invention, the prescription sales activity for a prescribing physician at prescription sales outlets including sampled prescription sales outlets and unsampled prescription sales outlets are estimated by generating signals representing distances among the prescription sales outlets, generating signals representing the size or total volume of prescription sales at each prescription sales outlet, selecting a group of sampled outlets closest to each unsampled outlet and forming an estimate of prescription sales for the prescribing physician at each sampled outlet according to the distances between the sampled outlet and the unsampled outlets associated with the sampled outlet by the selection and the size or total volume of the outlets. A signal representative of the prescription sales for the prescribing physician is produced according to the sales and estimates of sales for the prescribing physician at the sampled outlets.

In one embodiment of the invention, sales of a particular product are sampled at a first group of the pharmacies and are sent to a central station having a main processor and a group of work station processors. In the main processor, data representing the distances between the first group of pharmacies and each other pharmacy are generated and a signal representative of the total sales of all products of each pharmacy or the size of each pharmacy. A weighting factor for the sales of the particular product at each of the sampled pharmacies S in a neighborhood N(U) of the other pharmacy U is generated according to $$w_S = \{(1/d_S^q)/(\Sigma T_S/d_S^q)\} * T_u$$

where $d_S$ is the distance between sampled pharmacy S and one of the other pharmacies U, $T_S$ is the total sales volume for all products at sampled pharmacy S, $T_U$ is the total sales of all products at other pharmacy U, q is an number greater than 0 and the summation $\Sigma$ is over all sampled pharmacies S in the neighborhood N(U). The weighting factor signals, the sales data signals and the pharmacy characteristic signals are then transferred to a transfer store, divided therein and the divided portions are sent to a plurality of work station processors. The volume of the particular product at each pharmacy U is then estimated in the work station processors as $$V_U = \Sigma w_S V_S$$

where $V_S$ is the sales volume of the particular product at a selected sampled pharmacy, $w_S$ is the weighting factor for the selected sampled pharmacy and the summation $\Sigma$ is over all sampled pharmacies S in the neighborhood N(U).

In another embodiment of the invention, sales of a prescription product of a prescribing physician j are sampled at a first group of the pharmacies and are sent to a central station having a main processor and plural work station processors. At the main processor of the central station, data representing the distances $d_{SU}$ between the each of selected pharmacies S of the first group of pharmacies and each other pharmacy U is generated and a signal representative of the total sales of each pharmacy $T_S$ and $T_U$ is stored. A weighting factor for each sampled pharmacy in a neighborhood of an unsampled pharmacy is generated in the main processor and the sales data, the weighting factors and the pharmacy characteristics for the sampled pharmacies are transferred to a transfer store, divided therein and apportioned among the work station processors. The sales volume of the prescription product $V_j$ for the prescribing physician j is estimated in the work station processors for the prescribing physician j according to $$V_{Tj} = \Sigma_1 V_{Sij}\{1 + \Sigma_2 w_{SU}\}$$

where $V_{Sij}$ is the prescription product sales volume for physician j at pharmacy i, $w_{SU}$ is the weighting factor generated in the main processor associating sampled pharmacy S to a neighborhood related unsampled pharmacy U, $\Sigma_1$ is the summation over all sampled pharmacies and $\Sigma_2$ is the summation over weighting factors relating unsampled pharmacies p to sampled pharmacy Sij.

$$w_{SU} = \{(1/d_{SU}^q)/(\Sigma_3 T_S/d_{SU}^q)\} * T_U$$

where $\Sigma_3$ is the summation of over sampled pharmacies in a neighborhood of an unsampled pharmacy.

The features and advantages of the present invention will become apparent from the following detailed description of preferred embodiments thereof taken together with the accompanying drawings.

DETAILED DESCRIPTION

Figure 1:
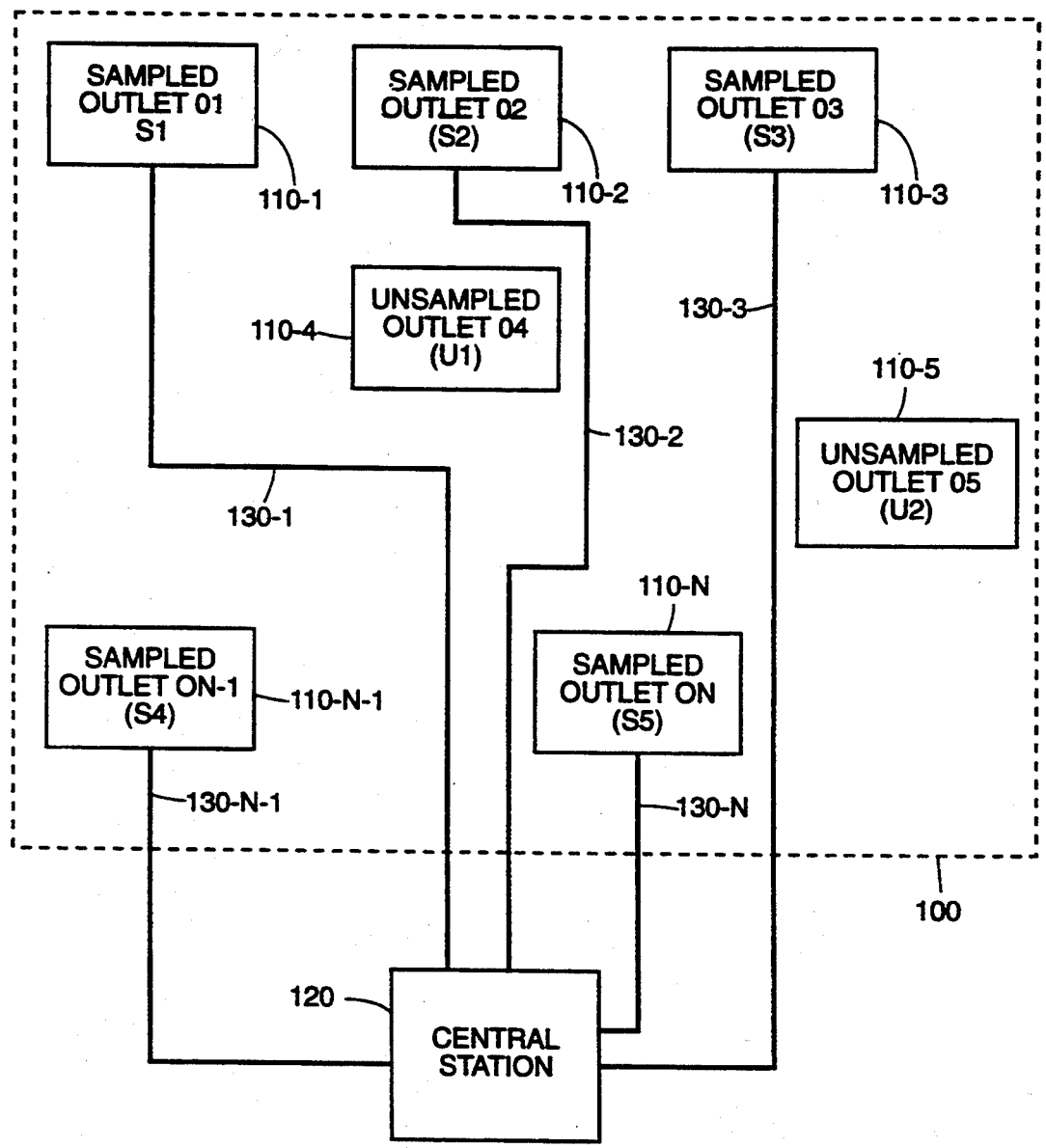
FIG. 1 is a block diagram showing an arrangement of sales outlets and a processing station illustrative of an embodiment of the invention.

FIG. 1 depicts an arrangement illustrating a first embodiment of the invention in which product sales at unsampled sales outlets are estimated. In FIG. 1, there are shown an area 100, sampled sales outlets 110-1, 110-2, 110-3, 110-N-1 and 110-N and unsampled sales outlets 110-4 and 110-5 in the area 100 and a central station 120. Each of sampled outlets 110-1, 110-2, 110-3, 110-N-1 and 110-N may preferably be coupled via a line of lines 130-1 through 130-N to the central station 120.

In FIG. 1, the outlets may be pharmacies or other type of retail stores or distribution establishments all of which distribute a particular product. The outlets are at various locations in the area 100. While there are 7 outlets shown in FIG. 1 for purposes of illustration, it is to be understood that there are generally hundreds or thousands of outlets which are not restricted to a given area. The location of each outlet is generally known in terms of latitude and longitude from available census data or in terms of zip code centroids from Post Office data. Accordingly, the distances between pharmacies can be determined. Product sales data generated at each outlet $S_n$ (e.g., 110-1) is preferably transferred to the central station 120 via a line (e.g., 130-1). Unsampled outlets $U_n$ (e.g., 110-4 or 110-5) in the area 100 are not coupled to the central station or, if coupled, do not supply valid sales data so that only an estimate of the sales volume of the particular product can be made.

A single area 100 is shown in FIG. 1 for purposes of illustration only. According to the invention, the estimation of sales activity at an unsampled outlet U is formed on the basis of the sales activity at the sampled outlets S in a neighborhood of the unsampled outlet U. The neighborhood of an unsampled outlet U may be defined as the N closest sampled outlets S which is different for each unsampled outlet and not as a predefined geographic area. In an urban area, the neighborhood of closest sampled outlets may all be located within a short distance of the unsampled outlet. In a rural area, the neighborhood of N closest sampled outlets nay spread over distances. Consequently, each unsampled outlet has its own neighborhood area which varies according to the distances to the nearest N sampled outlets. Advantageously, the correlation of sales activity data is not restricted to a predetermined geographic area as in the prior art.

Figure 2:
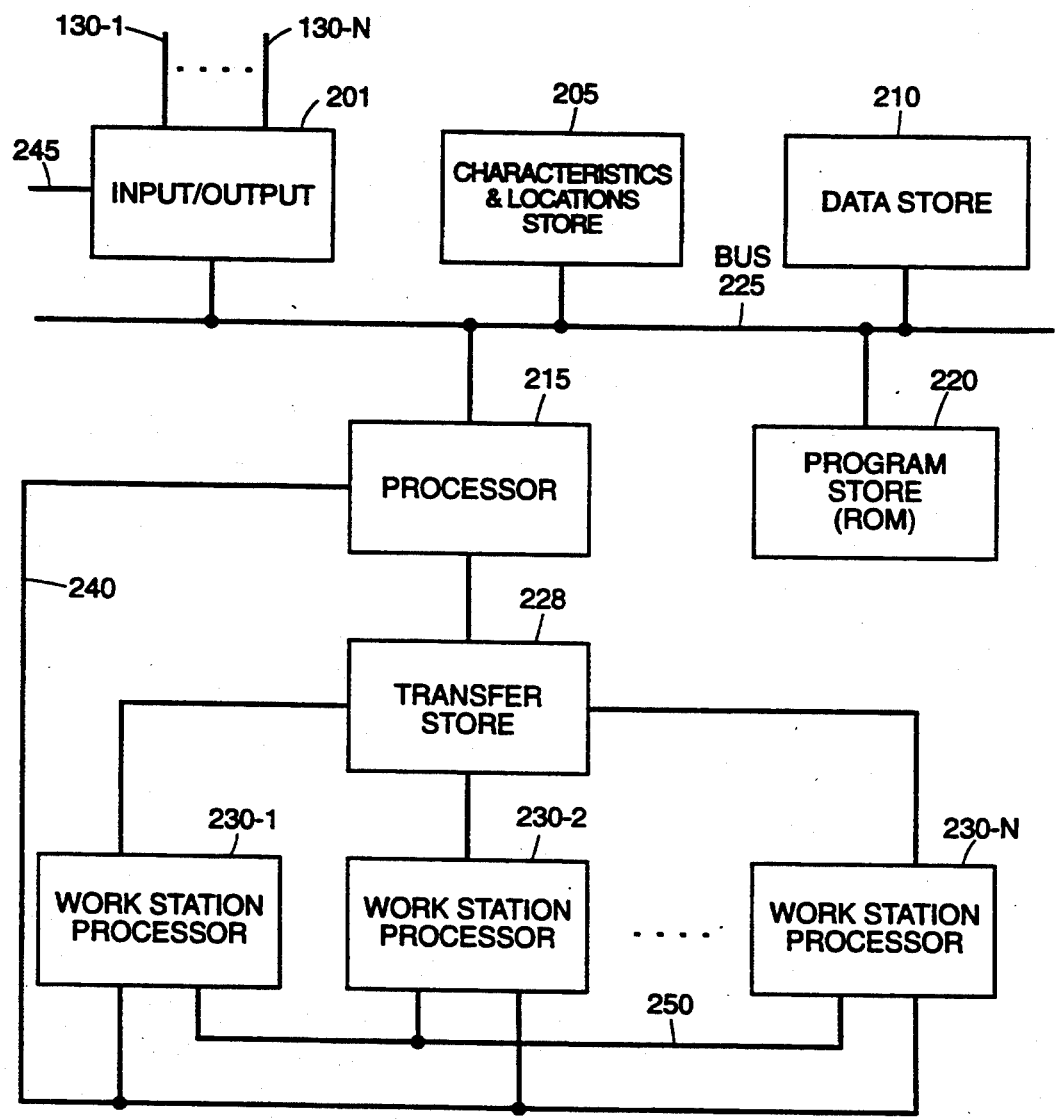
FIG. 2 is a block diagram of a processing system that may be used as the central station of FIG. 1.

FIG. 2 depicts a block diagram of the central station 120 of FIG. 1 which includes an input/output unit 201, a characteristics and location store 205, a sales data store 210, a processor 215, a program store 220, a bus 225, a transfer store 228 and work station processors 230-1 through 230-N. Input/output 201 is coupled to bus 225 and is also coupled to the sampled outlet lines 130-1 to 130-N and to output line 245. The characteristics and location store 205, the prescription data store 210 and the program store 225 are coupled to the bus 225. The Processor 215 is coupled to the bus 220, the transfer store 228 and is also coupled to work station processors via a control line 240. The transfer store 228 is coupled to work station processors 230-1 to 230-N and the work station processors are coupled together through a network 250. Characteristics signals stored in store 205 may include signals representing the type of outlet or the total sales of all products at the outlet. This type of data is available from sources such as Drug Distribution Data (DDD ™) available from IMS America, Plymouth Meeting, Pa. DDD ™ is a trademark of IMS America. Program store 220 stores instruction signals that control the operation of the processor 215 and provide parameter signals to determine the operation of work station processors 230-1 through 230-N through the processor 215 and control line 240.

The sales outlet data received by input/output 201 from sales outlets which may exceed $2 \times 10^9$ records each having between 88 and 1000 bytes is transferred to data store 210. In view of the large amount of data to be processed, the processing is divided between the processor 215 and the work station processors 230-1 through 230-N. Information signal arrays produced in the processor 215 are transferred to work station processors 230-1 through 230-N through the transfer store 228. Each information signal array from the processor 215 placed in the transfer store 228 is divided into N portions. A preassigned portion of the information signal array in the transfer store is supplied to each of work station processors 230-1 through 230-N and the processing of the portions in the work stations 230-1 through 230-N is controlled by signals from the processor 215 via the control line 240. After the processing of the information signal array portions in the work station processors, the processed information signal array portions are merged into one processed information signal array which is returned to transfer store 228 from the work station processors. The returned information signal array in the transfer store 228 is then further processed in the processor 215 to produce estimate sales volume results. The operation of the system of FIG. 2 will be further described in connection with the estimation arrangements shown in FIGS. 3–7.

Figure 3:
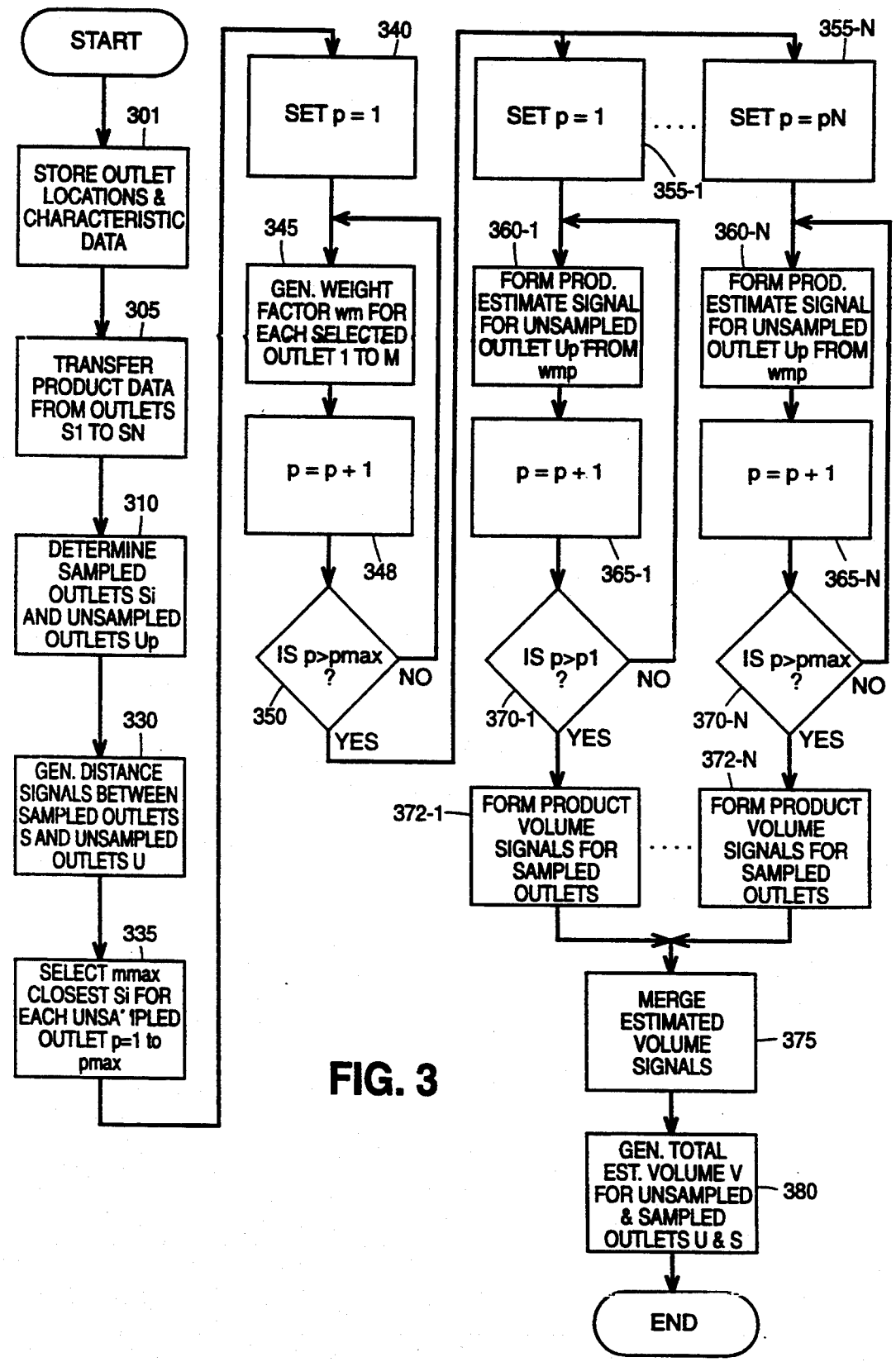
FIG. 3 is a flow chart showing the estimation of prescription sales at an outlet that is illustrative of the invention.

FIG. 3 depicts a flow chart illustrating the operation of the central station 120 of FIG. 1 in estimating the volume of sales of a particular product at an unsampled outlet such as outlet O4 or outlet O5 in FIG. 1. The operations depicted in the flow chart of FIG. 3 are performed by processor 215 and work station processors 230-1 to 230-N of FIG. 2 under control of instruction signals from in the program store 220. In the flow chart of FIG. 3, product data from outlets O1, O2, O3, ON-1 and ON are transferred to the input/output unit 201 preferably via corresponding lines 130-1 through 130-N in step 301. Transferred data is stored in outlet sales data store 210. A data transfer from an outlet may occur for each sales transaction or may include a number of transactions for a prescribed period of time. At preset intervals, the sales data is sent to processor 215 and therein is evaluated in step 310 to determine the sampled outlets Si and the unsampled outlets Up in the processor 215. Unsampled outlets may include outlets transferring data evaluated as invalid.

Figure 4:
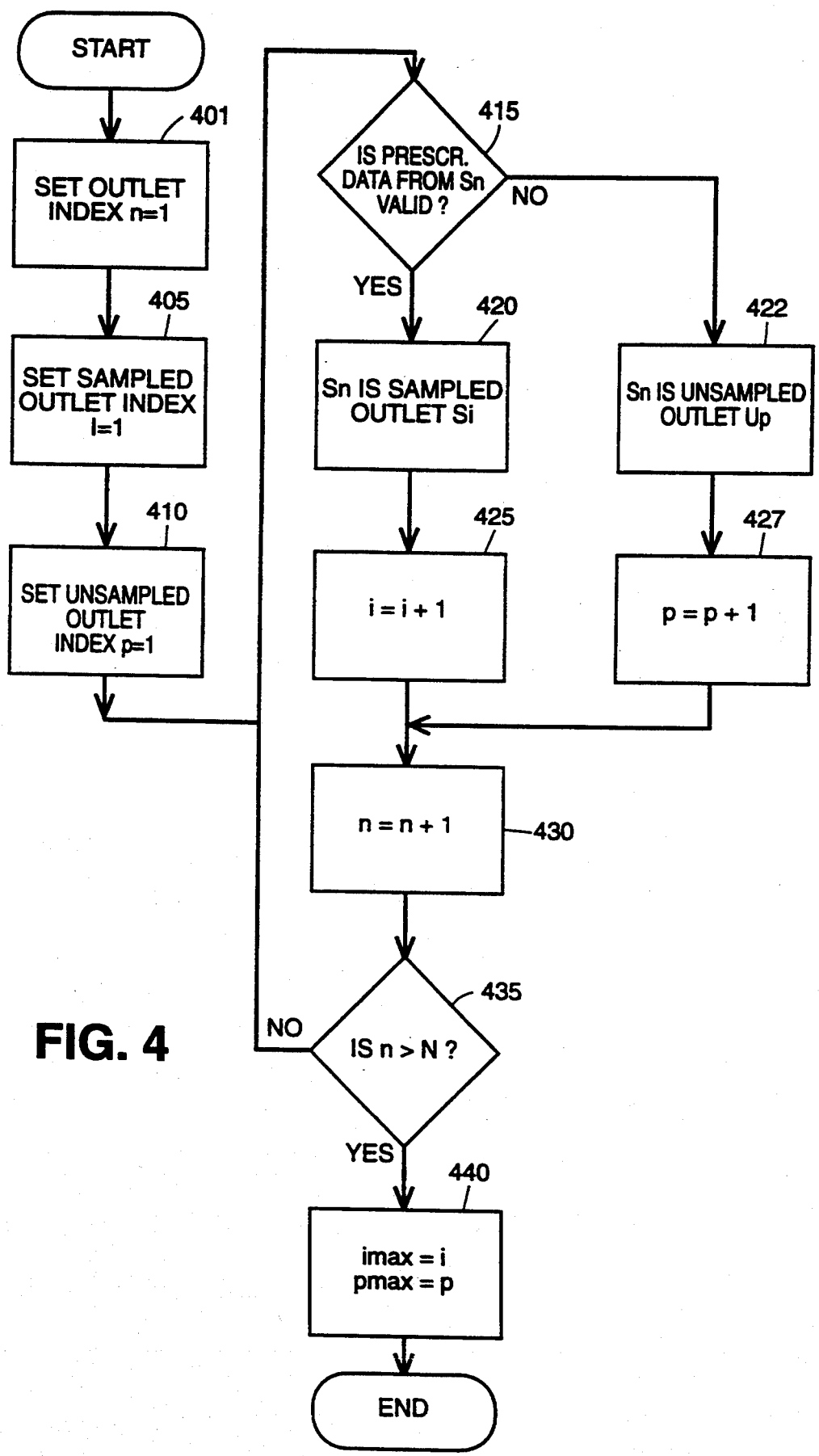
FIG. 4 is a flow chart showing the determination of sampled and unsampled outlets of FIG. 3 in greater detail.

FIG. 4 shows a method of determining sampled and unsampled outlets in greater detail. Referring to FIG. 4, an outlet index n for the outlets O1, O2, . . . , ON is set to 1 in step 401. A sampled outlet index i and an unsampled outlet index p are set to 1 in steps 405 and 410. The sales data for the particular product from each outlet On is checked in decision step 415 to determine if the data is valid (i.e., meets predetermined criteria). If the data is judged to be valid in step 415, the outlet On is classified as a sampled outlet Si in step 420 and the index i is incremented in step 425. When no data is available for the outlet On or the data is not accepted as valid in step 415, the outlet On is classified as an unsampled outlet Up in step 422 and the index p is incremented in step 427. The index n is then incremented in step 430. Until index n is greater than N for the last outlet ON, step 415 is reentered from decision step 435. When all of the outlets O1 through ON have been classified as sampled outlets and unsampled outlets, the last value of index p (pmax) and the last value of index i (imax) representing the number of unsampled outlets and the number of sampled outlets are stored in data store 210 (step 440).

As shown in FIG. 1, there are five sampled outlets 110-1 (O1), 110-2 (O2), 110-3 (O3), 110-N-1 (ON-1) and 110-N (ON) which are designated S1, S2, S3, S4 and S5 from the processing of FIG. 4 and two unsampled outlets 110-4 (O4) and 110-5 (O5) which are designated as U1 and U2 from processing of FIG. 4. Unsampled outlet U1 is located in the central portion of the area 100 and is surrounded by sampled outlets S1 through S5. Unsampled outlet U2 is located at one edge of the area 100, is closest to sampled outlet S5 and most remote from sampled outlet S1. Priorly known techniques based an estimate of the sales volume of a product at an unsampled outlet on the sales volume of the product for the geographic area. Since the sales outlets have different characteristics (e.g., size and location) and have sales related to outlets outside a particular area, estimates based on the overall sales volume in a particular area as in the prior art are biased. In accordance with the invention, an estimate of sales volume of a particular product at a sales outlet is based on the known sales volume of other outlets according to the distances between the sales outlet and the other outlets and the particular characteristics of the outlets independent of any geographic area. By using the outlet characteristics and the distances, an unbiased and more accurate estimate may be determined.

Signals corresponding to the distances between unsampled outlet U1 and sampled outlets S1 through S5 and the distances between outlet U2 and sampled outlets S1 through S5 are then formed in step 330. In step 335, the mmax closest sampled outlets to unsampled outlet p are selected. The selection is performed in the processor 215. mmax may be chosen according to the total number of sampled outlets. The selection of sampled outlets associated with each unsampled outlet is shown in greater detail in FIG. 5.

Figure 5:
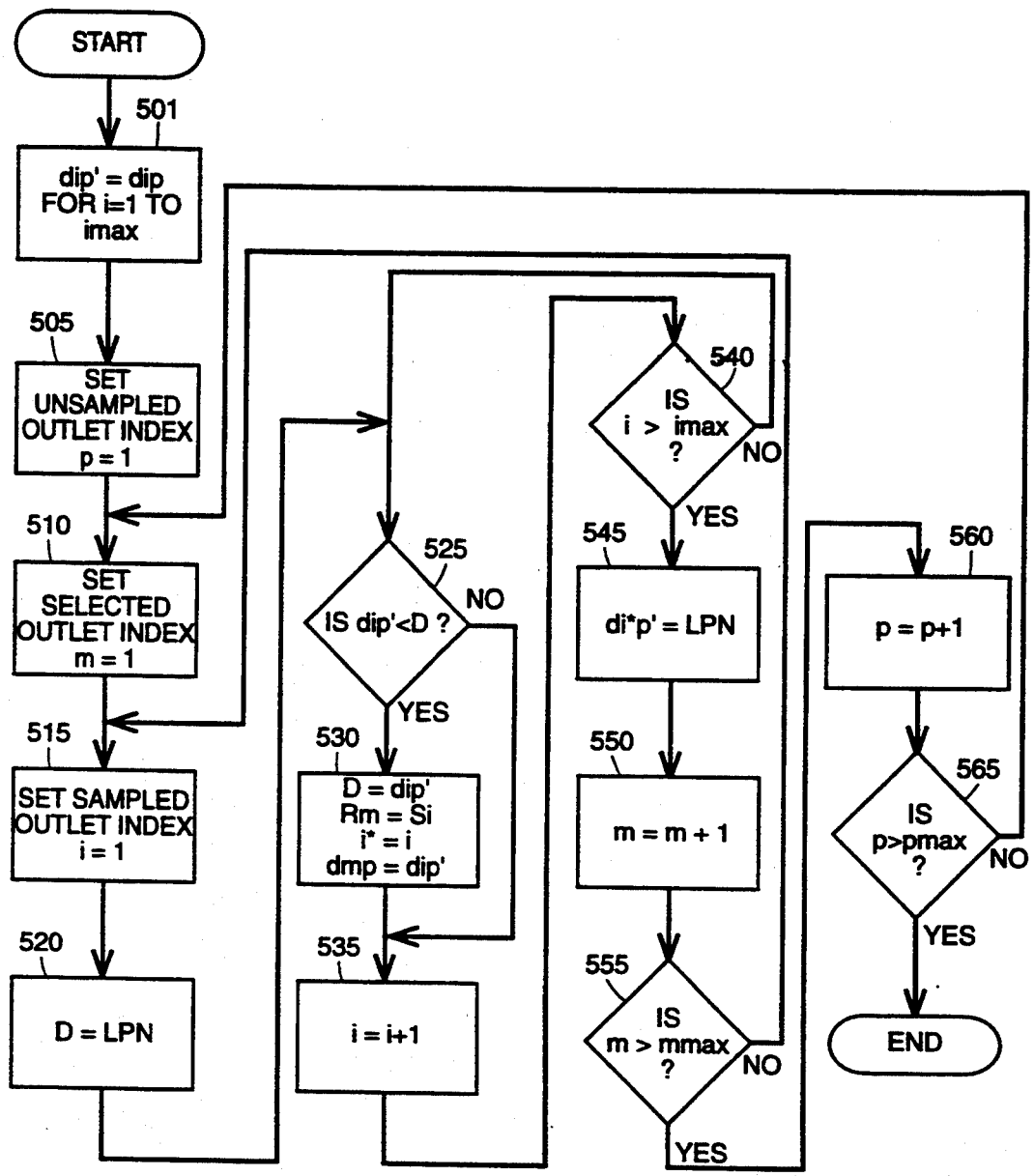
FIG. 5 is a flow chart showing the selection of the group of sampled outlets for each unsampled outlet in greater detail.

With reference to FIG. 5, a set of distance signals dip' for sorting is generated in step 501 corresponding to the distance signals dip generated in step 330. The unsampled outlet index p is set to one in step 505. A selected outlet index m is set to one in step 510 and the sampled outlet index i is set to one in step 515. In step 520, a signal D is set to LPN (largest possible number) and the loop including steps 525, 530, 535 and 540 is entered to find the smallest distance of the distances dip'.

In decision step 525, the signal dip' representing the distance from sampled outlet Si and unsampled outlet Up is compared to D. When dip' is less than D, D is set to dip', Rm representing a tentative selected outlet is set to Si, the index i* is set to i and a tentative selected distance signal dmp is set to dip' in step 530. Step 535 is then entered in which sampled outlet index i is incremented. Where dip' is not less than D, step 535 is entered directly from decision step 525. Decision step 540 is then entered. Until sampled outlet index i exceeds imax in step 540, step 525 is reentered to compare the next distance signal dip' to the last determined minimum distance signal. When i exceeds imax, the minimum of the selected sampled outlets is chosen as Rm. The minimum distance signal dip' is then set to LPN in step 545 to exclude Si* from comparison in step 525 and the selected outlet index m is incremented in step 550.

Step 515 is reentered from step 555 until mmax closest outlets for unsampled outlet p are selected and another outlet Rm is chosen in the loop from step 525 through 540. Upon selection of mmax sampled outlets, the unsampled outlet index p is incremented in step 560 and step 510 is reentered via decision step 565 so that a set of m sampled outlets may be selected for the next unsampled outlet Up in FIG. 5 via decision step 565. When p is greater than pmax, control is passed to step 340 in FIG. 3.

In step 340, index p is set to one. A weighting factor $w_m$ is then determined for each selected sampled outlet Rm of unsampled outlet Up in step 345. Weighting factor generation is performed in the processor 215. The weighting factor is an inverse function of the distance between the sampled outlet Rm and the unsampled outlet Up and the characteristics of the sampled and unsampled outlets according to $$w_m = \{(1/d_{R_mU_p}{}^q)/(\Sigma(T_m/d_{R_mU_p}{}^q))\} * T_{Up}$$

where $d_{R_mU_p}$ is the distance between sampled outlet Sm and unsampled outlet Up, the summation is over all sampled outlets for m=1 to mmax, $T_{Up}$ is the unsampled outlet characteristic (e.g., total sales volume for all products), $T_m$ is the sampled outlet characteristic and q is greater than zero. q may, for example, be 2. Index p is incremented in step 348 and control is passed to step 345 until p is greater than pmax in decision step 350.

The weighting factor signals for unsampled outlets Up and the product data for the outlets are read into the transfer store 228 as a data array which is divided therein into N data array portions. The processor 215 sends control signals to work station processors 230-1 through 230-N to initiate processing of the data file portions in the work station processor. Each work station processor then proceeds to form a product estimate signal for the data file portion assigned to it as indicated with respect to the entire data file in steps 355 through 370 in FIG. 3. In step 355-1, a starting value of the unsampled outlet index p=1 is set. The loop from step 360-1 to step 370-1 is then entered. The estimated sales of the particular product is then generated for a range of unsampled stores Up in step 360 according to $$\text{Est } (V_{Up}) = \Sigma w_m V_m$$

where $V_m$ is the sales volume of the particular product at sampled outlet m and the summation is over the sampled outlets from m=1 to m=mmax. The unsampled outlet index p is incremented in step 365-1 and control is passed back to step 360-1 via decision step 370-1 until p is greater than the maximum of the range processed in work station processor 230-1 and an estimate of sales volume for all unsampled outlets in the range has been formed. The processing of the other work station processors 230-2 through 230-N is the same as described with respect to the work station processor 230-1 except that the range is determined by the portion of the data file sent to the work station. The processing in the work station processor 230-N is shown in the steps 355-N through 370-N.

For purposes of illustration with respect to FIG. 1, the number of selected sampled outlets mmax is chosen as 3. It is to be understood, however, that other values may be chosen. For example, if there are 50 or more sampled outlets, mmax=10 is a suitable value. In FIG. 1, sampled outlets O1, O2 and O3 are selected as the three closest sampled outlets R1, R2 and R3 to unsampled outlet U1. To illustrate the invention, assume that the distance $d_{R1U1}$ from sampled outlet R1 to unsampled outlet U1 is 0.4 miles, the distance $d_{R2U1}$ between sampled outlet R2 and unsampled outlet U1 is 0.2 miles and the distance $d_{R3u1}$ between sampled outlet R3 and unsampled outlet U1 is 0.6 miles. Further assume that the total sales volume for all products at sampled outlets R1, R2, R3 and U1 are $3,000, $2,000, $5,000 and $4,000, respectively. The weighting factor for sampled outlet R2 is then $$w_2 = \{(1/0.2)^2/(2000/(0.2)^2 + 3000/(0.4)^2 + 5000/(0.6)^2)\} * 4000$$

$$w_2 = 1.210084$$

Similarly, $w_1 = 0.302521$ and $w_3 = 0.13445377$. For a sales volume of the particular product at R1, R2 and R3 of 5, 20 and 4, respectively, the estimated sales volume of the particular product at unsampled outlet U1 is $$\text{Est}(V_{U1}) = w_1 * v_{R1} + w_2 v_{R2} + w_3 v_{R3}$$

$$\text{Est } (V_{u1}) = 26.252$$

The product volume signals for the sampled outlets Si is then formed in step 372-1 through 372-N and the total estimated sales volume of the product for unsampled and the sampled outlets is then formed for each range in the work station processors 230-1 through 230-N in steps 375. The resulting unsampled outlet estimate and total volume estimate signals of the processing in the work station processors is then merged in and totalled step 380 into a result data file. The result data file is transferred to transfer store 228 and therefrom to data store 210. The results are then sent to output line 245 of the input/output 201.

Figure 6:
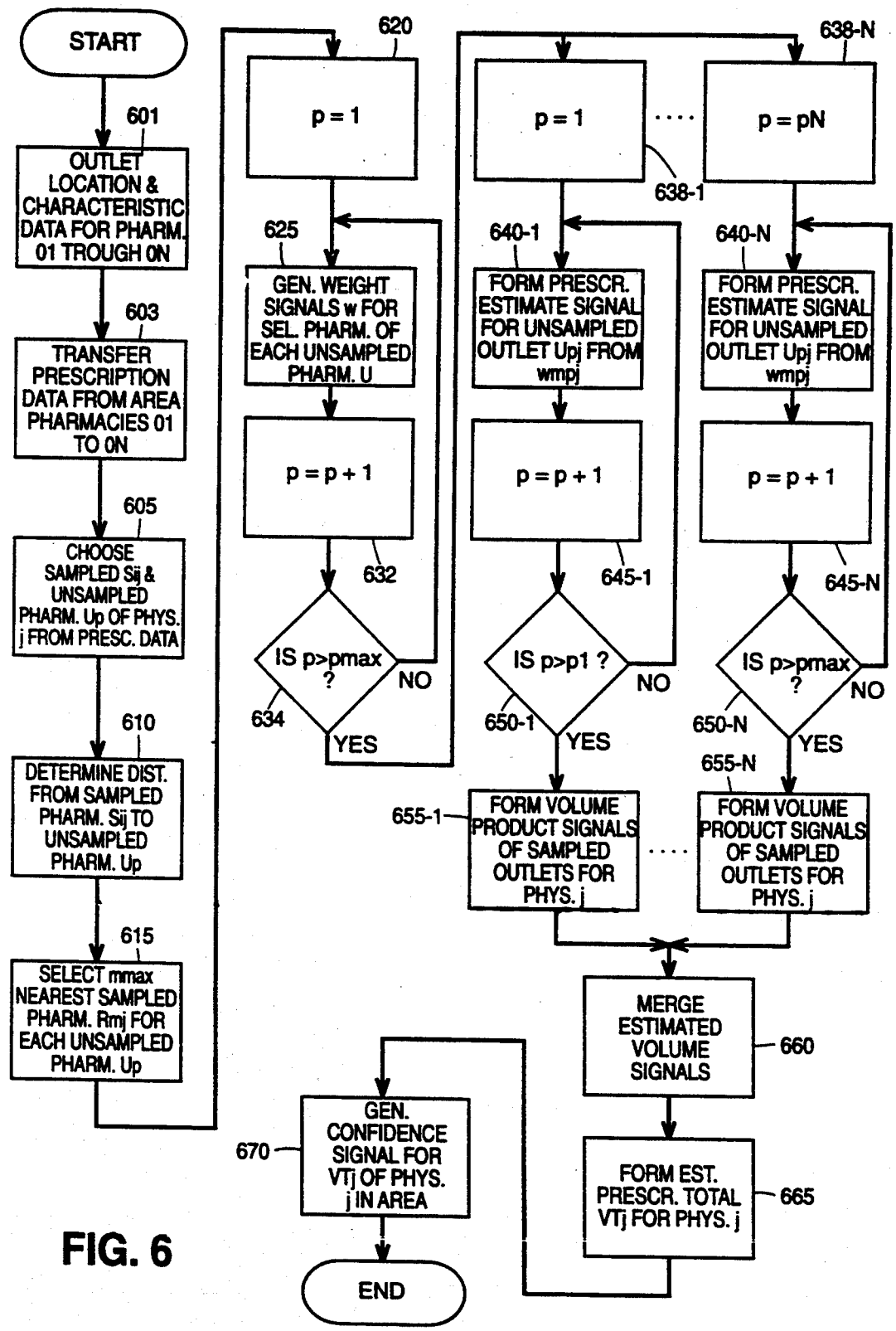
FIG. 6 is a flow chart showing one arrangement for the estimation of prescriptions sales for a prescribing physician at a plurality of pharmacies illustrative of the invention.

FIG. 6 shows a flow chart illustrating estimation of the distribution of a controlled product by a control authority. More particularly, FIG. 6 shows the operation of the arrangement of FIGS. 1 and 2 in estimating sales of a prescription product for a prescribing physician at the pharmacies. The operations in the flow chart of FIG. 6 are performed by processor 215 and work station processors 230-1 through 230-N of FIG. 2 under control of corresponding instruction signals stored in the program store 220. Referring to FIG. 6, location data, data of type characteristics of pharmacy outlets O1 through ON in FIG. 1 and physician identification data are stored in the characteristics and locations store 205 of FIG. 2 in step 601. Prescription data is transferred from pharmacies O1, O2, O3, ON-1 and ON is stored in pharmacy outlet data store 210 according to the prescribing physicians (step 603).

At prescribed intervals, the total sales for the prescribing physician j of a particular prescription product is estimated in steps 605 through 670 of FIG. 6. In step 605, the processor 215 operates to determine the sampled pharmacy outlets Sij and the unsampled pharmacy outlets Up for a particular prescription product according to the validity and volume of the transferred prescription data of the prescribing physician j. The arrangement shown in FIG. 4 may be used in the determination of step 605. As described with respect to FIGS. 1 and 3, pharmacy outlets O1, O2, O3, ON-1 and ON can be determined as sampled outlets S1j, S2j, S3j, S4j and S5j where the sampled data is validated. Outlets O4 and O5 are classified as unsampled outlets U1 and U2.

Step 610 is entered from step 605 and signals representative of the distances dip between each sampled outlet Sij and each unsampled outlet Up are generated in the processor 215. After the distance determination of step 610, the set of nearest sampled pharmacy outlets Rmj for each unsampled pharmacy outlet Up is selected by processor 215 according to step 615. Selection of sampled pharmacies may be performed as described with respect to FIG. 5. Then, the unsampled pharmacy outlet index p is set to 1 in step 620 and a weighting factor signal wm for the each sampled pharmacy outlet Rm (m=1 to mmax) is generated in loop from step 625 to step 634. Each weighting factor signal is formed according to $$w_m = \{(1/d_{R_mU_p}{}^q)/(\Sigma(T_{Rm}/d_{R_mU_p}{}^q))\} * T_{Up}$$

where q is greater than 0, $T_{Up}$ is the total sales volume of all products at pharmacy outlet Up, $T_{Rm}$ is the total sales volume of all products at pharmacy outlet Rm and the summation $\Sigma$ is from m=1 to mmax.

After the weighting factor signals have been formed for the last unsampled pharmacy in the loop from step 625 to 634, a data array including the weighting information and the sales data from store 210 is formed by the processor 215 and sent to transfer store 228. The data array is divided into N portions each of which is processed by one of work station processors 230-1 through 230-N to form a signal representing an estimate of the total prescription product sales volume for physician j. The operations of the work station processors are controlled by the processor 215 through the control line 245. Each work station processor operates to process a predetermined range of the data array in the transfer store 228.

The work station processor 230-1 operates according to steps 638-1 through 655-1 to form the volume product signals for physician j in the range p=1 to p=p1. In step 640-1, the prescription estimate signal for unsampled outlets Upj is formed for each unsampled pharmacy in the range from p=1 to p=p1 and the sales volume signal for the sampled pharmacies in this range is determined by the work station processor 230-1 according to step 655-1. Work station processor 230-N operates in similar manner for physician j over the range p=pN to p=pmax as indicated in FIG. 6 according to steps 638-N through 655-N. Signals are transferred from one work station processor to another as required for the operation of the one work station processor through the network 255. The results of the operation of work station processors 230-1 through 230-N are merged in step 660 and an estimate of the prescription product volume $$V_T = \Sigma_1 V_{Sij} + \Sigma_2 V_{jUp}$$

is generated in step 665 where $$V_{jUp} = \Sigma_3 \{ \{ (1/d_{RmUp}{}^q)/(\Sigma_3(T_{Rm}/d_{RmUp}{}^q) \} \cdot T_{Up} \} V_{Rmj}$$

$\Sigma_1$ is the summation over all sampled outlets, $\Sigma_2$ is the summation over all unsampled outlets, $\Sigma_3$ is the summation over all sampled outlets in the neighborhood of unsampled outlet Up. At this time, a confidence signal that estimates the degree of possible error of the total volume $V_{Tj}$ of the product prescriptions of the prescribing physician j is then generated in step 670.

Figure 7:
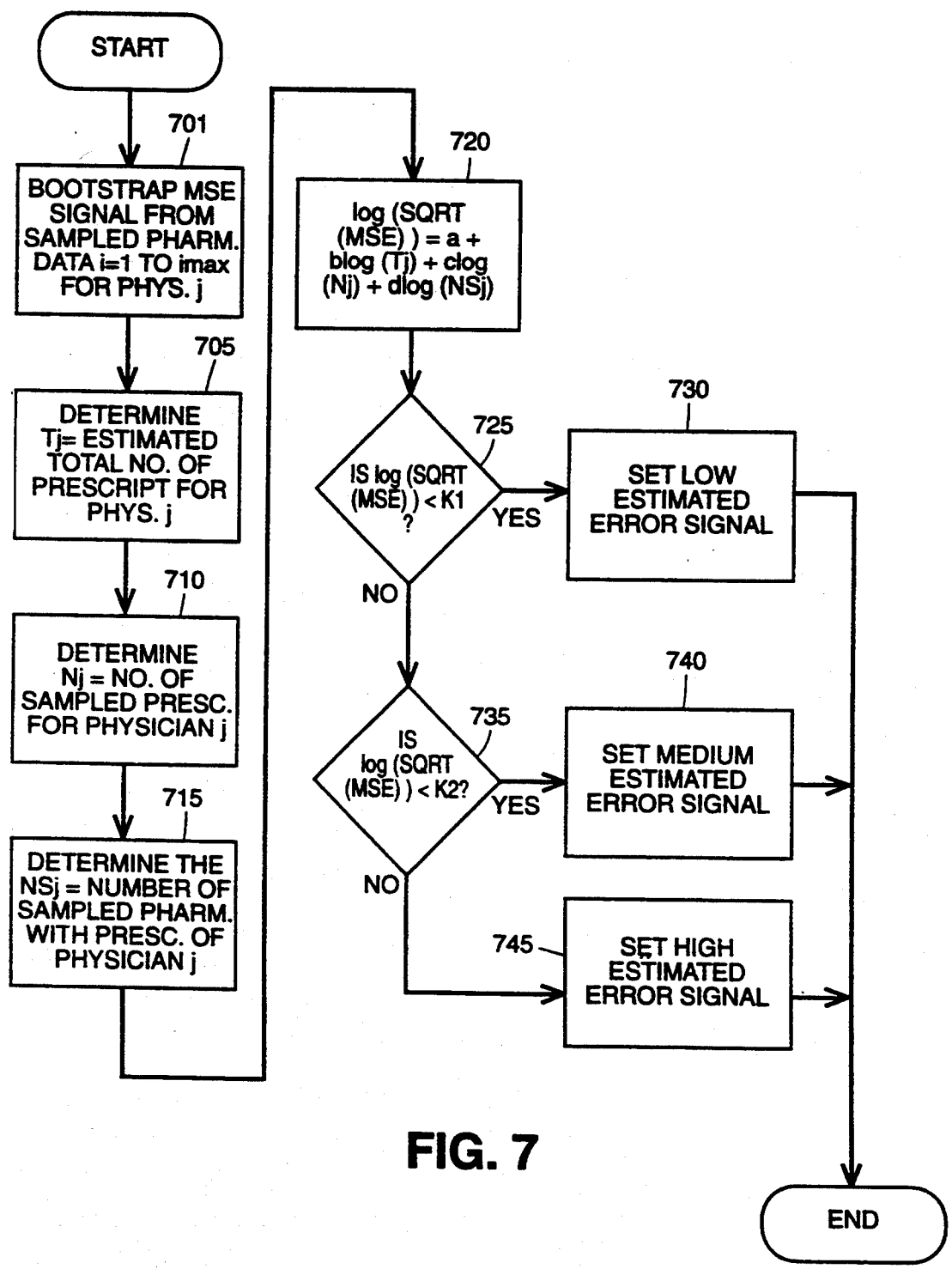
FIG. 7 is a flow chart showing the confidence signal operation of FIG. 6 in greater detail.

FIG. 7 shows the confidence signal generation operation of step 670 in greater detail. Referring to FIG. 7, a mean squared error signal MSE is first generated by bootstrapping on the basis of the sales data from the sampled pharmacy outlets S1 through Simax in step 701. The bootstrapping method is well known in the art and is described in "The Jacknife, The Bootstrap, and Other Resampling Plans" by B. Efron, Society for Industrial and Applied Mathematics (SIAM) Publications, Philadelphia 1982.

In the bootstrapping, subsets of pharmacy outlets are selected and the prescribing physician's prescription volume is estimated therefrom. The variances of the "bootstrapped" estimates closely approximates the true variance. A generalized variance function (GVF) is derived from the MSEs generated in step 701 of the form $$\log(\text{SQRT}(\text{MSE})) = a + b\log(T_j) + c\log(N_j) + d\log(N_{Sj})$$

where SQRT is the square root, a, b, c and d are regression coefficients, $T_j$ is the estimated total of the prescription product prescribed by physician j, $N_j$ is the total of prescription products prescribed by physician j and dispensed at the sampled pharmacy outlets and $N_{Sj}$ is the number of sampled pharmacy outlets with prescription product sales for physician j. The generalized variance function is described in "Introduction to Variance Estimation" by K. M. Wolter, Springer-Verlag, New York 1985.

The values of $T_j$, $N_j$ and $NS_j$ are determined in steps 710, 715 and 720 from the prescription data in store 210 of FIG. 2 in processor 215. Regression coefficient signals a, b, c and d are generated by multiple regression techniques well known in the art and a log(SQRT(MSE)) value for the physician j is determined in step 720. Decision step 725 is then entered in which the value log(SQRT(MSE)) is compared to K1. If log(SQRT(MSE)) is less than K1, a low estimated error signal is produced in step 730. The value log(SQRT(MSE)) is then compared to K2>K1 in step 735 to produce a medium estimated error signal in step 740 if log(SQRT(MSE)) is less than K2. Where log(SQRT(MSE)) is not less than K2, a high estimated error signal is generated in step 745. While three values for the estimated error signal are determined in the flow chart of FIG. 7, it is to be understood that any number of values such of 5 may be used.

Figure 8:
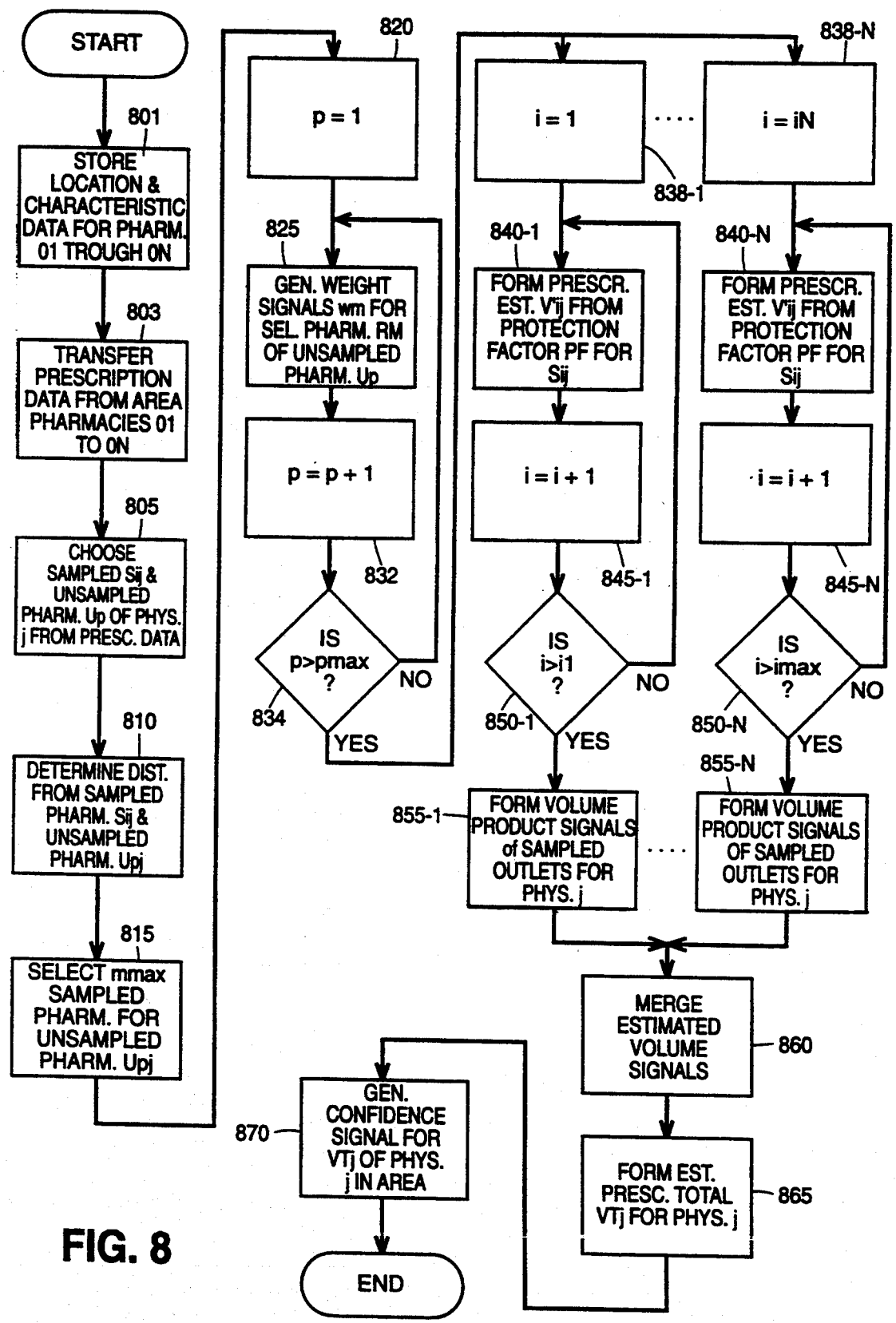
FIG. 8 is a flow chart showing another arrangement for the estimation of prescription sales for a prescribing physician at a plurality of pharmacies illustrative of the invention.

The flow chart of FIG. 8 illustrates another arrangement for estimating the prescription product sales volume of a prescribing physician. According to the arrangement of FIG. 8, a group of sampled pharmacies is selected for each unsampled pharmacy and a weighting factor for each sampled pharmacy in the neighborhood of one of the unsampled pharmacies is generated as in FIG. 6. The weighting factors for the sampled pharmacies are combined with the actual sales data for the sampled pharmacies according to $$V_{Tj} = \Sigma_1 V_{Sij} + \Sigma_2 \Sigma_3 w_{sp} V_{Sij}$$

which corresponds to $$V_{Tj} = \Sigma_1 V_{Sij}[1 + \Sigma_4 w_{ip}]$$

where $V_{Sij}$ is the prescription product sales volume for physician j at pharmacy i, $w_{ip}$ is the weighting factor for a sampled pharmacy i in the selected neighborhood of unsampled pharmacy p, $\Sigma_1$ is the summation over all sampled pharmacies and $\Sigma_2$ is the summation over all unsampled pharmacies, $\Sigma_3$ is the summation of all sampled pharmacies in the neighborhood of unsampled pharmacy p and $\Sigma_4$ is the summation of weighting factors associated with sampled pharmacy i. The resulting estimate of sales volume for the prescribing physician is similar to that described with respect to FIG. 6 but the efficiency of the estimate generation is improved.

In the method of FIG. 8, the sampled pharmacies in the neighborhood of each sampled pharmacy are first determined and the weighting factor signals $w_{ip}$ for the neighborhood sampled pharmacies are formed in the processor 215 of FIG. 2 on the basis of the pharmacy location, the characteristics data and the physician identification data in store 205. The sales data from the sampled pharmacies and the weighting factor signals $w_{ip}$ are transferred to the transfer store 228, divided therein into prescribed ranges and each range of data is supplied to an assigned one of the work station processor 230-1 through 230-N. In each work station processor, the estimated sales volume for each sampled pharmacy outlet in range processed by the work station processor is generated from the sales data and the projection factor for the sampled pharmacy outlet. The total estimated sales volume for the sampled pharmacy outlets over range of the work station processor is then generated. When the work station processing is completed the resulting estimated sales volumes from the work station processors are merged and transferred via the transfer store 228 to the processor 215.

Referring to FIG. 8, the locations, type characteristics of pharmacy outlets O1 through ON in FIG. 1 and physician identification data are stored in the characteristics and locations store 205 of FIG. 2 in step 801. Prescription data is received from the pharmacies O1, O2, O3, ON-1 and ON and is stored in data store 210 according to the prescribing physicians (step 803).

The total sales for the prescribing physician j of a particular prescription product is estimated in steps 805 through 870. In step 805, the processor 215 operates to identify the sampled pharmacy outlets Sij and the unsampled pharmacy outlets Up for a particular prescription product according to the validity and volume of the transferred prescription data of the prescribing physician j. The arrangement shown in FIG. 4 may be used. As described with respect to FIGS. 1 and 3, pharmacy outlets O1, O2, O3, ON-1 and ON can be determined as sampled outlets S1j, S2j, S3j, S4j and S5j where the sampled data is validated. Outlets O4 and O5 are classified as unsampled outlets U1 and U2.

Step 810 is entered from step 805 and signals representative of the distances dip between each sampled outlet Sij and each unsampled outlet Up are generated in the processor 215. After the distance determination of step 810, the set of nearest sampled pharmacy outlets Rmj for each unsampled pharmacy outlet Up is selected by processor 215 according to step 815. The selection of sampled pharmacies Rmj may be performed as previously described with respect to FIG. 5.

The unsampled pharmacy index p is reset to one in step 820 and weighting signals wmp are formed for the selected sampled pharmacies Rmi in the loop from step 825 to 834. In step 825, the weighting signal $$w_{mp} = \{(1/d_{RmUp}^q)/(\Sigma(T_m/d_{RmUp}^q)\} * T_{Up}$$

is formed for each sampled pharmacy m selected as in the neighborhood of sampled pharmacy Up. After the weighting signals for all unsampled pharmacies are formed in the processor 215, the sales data stored in store 210 and the weighting signals are transferred to transfer store 228 wherein the data and weighting signal array is divided into N portions and each portion is transferred to one of work station processors 230-1 through 230-N. The processing of the portion transferred to work station processor 230-1 is shown from step 838-1 through 855-1 in FIG. 8 and the processing the portion transferred to work station processor 230-N is indicated from step 838-1 to 838-N.

With respect to the processing of the range of sampled pharmacies in work station processor 230-1, the sampled pharmacy index i is set to one in step 838-1 and the loop from step 840-1 through 850-1 is iterated to form the estimated prescription volume $V'_{ij}$ for the sampled pharmacies in the range from i=1 to i=i1. In each iteration, an estimated volume signal is generated for sampled pharmacy i in step 840 according to $$VT_{Sij} = V_{Sij}[1 + \Sigma w_{mp}]$$

where $V_{Sij}$ is the actual prescription product sales volume for physician j at pharmacy i, $w_{mp}$ are the weighting factor for sampled pharmacy Sij and $\Sigma$ is the summation over all weighting factors associated with the pharmacy Sij. $[1 + \Sigma w_{mp}]$ is a projection factor for a physician's prescription at the sampled pharmacy $V_{Sij}$.

After the estimated volume signal is formed for the range i=1 to i1 in the work station processor 230-1, step 855-1 is entered from step 850-1 wherein the total volume for the range from i=1 to i=i1 by summing the estimated volumes for the pharmacies Sij. The work station processor 230-N operates in similar manner from step 838-N to 855-N to generate a total estimated volume for the range from iN to imax. Work station processors are interconnected by the network 250 such as an ethernet or token ring arrangement so that signals from one work station processor that are required for the formation of the $VT_{TSij}$ signal in another work station are transferred. The total volume signals for the ranges are merged in step 860 and the merged signals are transferred to the processor 215 via the transfer store 228. The resulting estimated total volume signal $V_{Tj}$ for the physician j is then formed in the processor 215 (step 865) and a confidence signal for the estimated total volume $V_{Tj}$ is generated in step 870 as described with respect to the flow chart of FIG. 7.

The invention has been described with respect to particular illustrative embodiments. It is to be understood that the present invention is not limited to the above described embodiments and that various changes and modifications may be made by those of ordinary skill in the art without departing from the spirit and scope of the invention.

What is claimed is:

1. A system for estimating distribution of a product at distribution locations including a plurality of locations at which product distribution information is sampled and at least one other location comprising:

means for receiving distribution information from each of the plurality of sampled locations;

first processing means for generating a first plurality of signals each characterizing one of the plurality of sampled locations and the at least one other location and a second plurality of signals each corresponding to a distance between the at least one other location and one of the sampled locations in a prescribed neighborhood of the at least one other location;

means for partitioning the received distribution information from the sampled locations, the distance corresponding signals and the characterizing signals into sets, each set corresponding to a group of the plurality of distribution locations;

second processing means comprising a plurality of second processors and a network for exchanging information among said second processors, each second processor being responsive to one of the sets of distribution information, distance corresponding signals, characterizing signals and the information from the information exchange network for forming a signal representing an estimate of the product distribution of one group of the plurality of distribution locations by combining the received distribution information, the distance corresponding signals and the characterizing signals.

2. A system according to claim 1, wherein the partitioning means comprises:
- a store for storing the received distribution information, the distance corresponding signals and the characterizing signals from the first processing means;
- means for dividing the stored distribution information, the distance corresponding signals and the characterizing signals from the first processing means into the sets; and
- means for transferring each of the sets from the dividing means to one of the second processors.

3. A system according to claim 1, wherein the first processing means is responsive to the estimate signals formed in the second processing means for combining the estimate signals to generate a signal representing an estimate of the product distribution for the plurality of locations and the at least one location.

4. A system according to claim 1 wherein the at least one other location comprises a plurality of unsampled locations U and the combining of received distribution information, the distance corresponding signals and the characterizing signals includes combining signals $V_S$ representing product distribution volume at each of the plurality of sampled locations S of the group, signals $T_S$ characterizing each of the plurality of sampled locations S of the group, signals $d_{SU}$ representing distances between one of the unsampled locations U of the group and each of the plurality of sampled locations S within the prescribed neighborhood of the unsampled location to generate a signal $V_U$ corresponding to an estimate of product distribution at the unsampled locations of the group according to $$V_U = \Sigma_2 \{ ((1/d_{SU}^q)/(\Sigma_1 T_S/d_{SU}^q)) * T_U \} V_S$$

where q is greater than zero, $\Sigma_1$ is a summation over the plurality of sampled locations and $\Sigma_2$ is a summation over the unsampled locations.

5. A system for estimating distribution of a product at distribution locations including a plurality of locations at which product distribution information is sampled and at least one other location comprising:
- means for receiving distribution information from each of the plurality of sampled locations;
- first processing means for generating a plurality of signals each characterizing one of the plurality of sampled locations and the at least one other location;
- means for partitioning the received distribution information from the sampled locations and the characterizing signals into sets, each set corresponding to a group of the plurality of distribution locations;
- second processing means comprising a plurality of second processors and a network for exchanging information among said second processors,
- each second processor being responsive to one of the sets of distribution information and characterizing signals and the information from the exchange network for forming a signal representing an estimate of the product distribution of one group of the plurality of distribution locations by combing the received distribution information with the characterizing signals, wherein the characterizing signals include signals representing the distances between the sampled locations and the at least one other location.

6. A system according to claim 5, wherein the at least one other location includes a plurality of unsampled locations and the received distribution information and the characterizing signals for each group are combined according to $$V_T = \Sigma_1 V_{Si}[1 + \Sigma_2 w_{su}]$$

where $V_T$ is the total estimated product distribution volume of the group, $V_{Si}$ is the product distribution volume for a sampled location i of the group, $w_{su}$ is a weighting factor for a sampled location s in a selected neighborhood of the unsampled locations u of the group, $\Sigma_1$ is the summation over all sampled locations of the group and $\Sigma_2$ is the summation over the weighting factors associated with the sampled locations Si of the group and $$w_{su} = \{(1/d_{su}^q)/(\Sigma_3 T_S/d_{su}^q)\} * T_U$$

where $d_{su}$ is the distance between a selected sampled location s and a selected unsampled location u, $T_S$ is a signal characterizing the selected sampled locations, $T_U$ is a signal characterizing the selected unsampled location u, q is a number greater than zero and $\Sigma_3$ is the summation over all sampled locations of the group in a neighborhood of the unsampled location u.

7. A system according to claim 6, wherein each of the sampled and unsampled locations is a pharmacy, the characterizing parameter $T_S$ represents a size of the sampled pharmacy S and the characterizing parameter $T_U$ represents a size of the unsampled pharmacy U.

8. A system according to claim 5, wherein a plurality of sources j distribute the product, the at least one other location includes a plurality of unsampled locations and the received distribution information and the characterizing signals for each source j are combined according to $$V_{TJ} = \Sigma_1 V_{Sij}[1 + \Sigma_2 w_{su}]$$

where $V_{Tj}$ is the total estimated product distribution volume for the source j for the group, $V_{Sij}$ is the product distribution volume for source j at a sampled location i of the group, $w_{su}$ is the weighting factor for a sampled location s in a selected neighborhood of the unsampled location u, $\Sigma_1$ is the summation over all sampled locations and $\Sigma_2$ is the summation over the weighting factors associated with sampled locations Sij, and $$w_{su} = \{(1/d_{su}^q)/(\Sigma_3 T_S/d_{su}^q)\} * T_U$$

where $d_{su}$ is the distance between a sampled location s and one of the unsampled locations u, $T_S$ is a signal characterizing the sampled location, $T_U$ is a signal characterizing the unsampled location u, q is a number greater than zero and $\Sigma_3$ is the summation of all sampled locations s in a neighborhood of the unsampled location u.

9. A system according to claim 8, wherein the product is a prescription medicine, each source is a prescription medicine prescriber, each of the sampled and unsampled locations is a pharmacy, the characterizing signal $T_S$ represents a size of the sampled pharmacy S and the characterizing signal $T_U$ represents a size of the unsampled pharmacy U.

10. A system according to claim 5, wherein the partitioning means comprises:
- a store for storing the received distribution information and the characterizing signals from the first processing means;
- means for dividing the stored distribution information and the characterizing signals into the sets; and
- means for transferring the sets from the dividing means to the second processors.

11. Apparatus for estimating distribution of a product by a distributing authority at a plurality of first distribution locations at which distribution information of the distributing authority is sampled and second distribution locations, comprising:
- means for receiving distribution information of the distribution authority from each first distribution location;
- first processing means responsive to predetermined characteristics of each of the first and second distribution locations for Generating a plurality of signals each representative of a factor by which the second distribution locations affect distribution at each first distribution location and for generating a plurality of signals each representative of the distance between each second distribution location and each first distribution location in a prescribed neighborhood of the second distribution location;
- means for partitioning the distribution information of the distribution authority from the first distribution locations, the factor signals and the distance signals into sets each corresponding to a group of first distribution locations;
- second processing means including a plurality of work station processors and an information exchange network for exchanging information among the work station processors, each work station processor being responsive to one of the sets of distribution information, factor signals and the distance signals from the partitioning means and information from the information exchange means for forming a signal representing an estimate of the product distribution of the distribution authority at one of the groups of distribution locations.

12. Apparatus according to claim 11 wherein said partitioning means comprises:
- means for storing the distribution information received from the first distribution locations and the factor and distance signals from said first processing means; and
- means for dividing the stored distribution information and the factor signals into first distribution location groups.

13. Apparatus according to claim 11 wherein said first processing means is responsive to the estimate signals formed in the work station processors for generating a signal representative of an estimated product distribution of the controlling authority.

14. Apparatus according to claim 13, wherein the controlled product is a prescription medicine, the distribution locations are pharmacies and the controlling authority is a prescription prescriber.

15. Apparatus according to claim 11, wherein the controlled product is a prescription medicine, the distribution locations are pharmacies and the controlling authority is a prescription prescriber.

* * * * *

UNITED STATES PATENT AND TRADEMARK OFFICE
CERTIFICATE OF CORRECTION

PATENT NO. : 5,420,786

DATED : May 30, 1995

INVENTOR : MARK A. FELTHAUSER, ET AL.  Page 1 of 2

It is certified that errors appear in the above-identified patent and that said Letters Patent is hereby corrected as shown below:

ON THE TITLE PAGE

[56] References Cited

Other Publications, "SOurces," should read --Sources,--.

DRAWING

Sheet 6, Fig. 6, "TROUGH" should read --THROUGH--; and

Sheet 8, Fig. 8, "TROUGH" should read --THROUGH--.

COLUMN 6

Line 21, "nay" should read --may--; and

Line 37, "Processor" should read --processor--.

COLUMN 10

Line 4, "$Est(V_{U1})=w_1*v_{R1}+w_2V_{R2}+w_3V_{R3}$" should read --$Est(V_{U1})=w_1*v_{R1}+w_2V_{R2}+w_3V_{R3}$--.

COLUMN 11

Line 43, "$*T_{Up}\{V_{Rmj}$" should read --$*T_{Up}\}V_{Rmj}$--.

COLUMN 12

Line 32, "such of" should read --such as--.

COLUMN 13

Line 61, "processing" should read --processing of--.

UNITED STATES PATENT AND TRADEMARK OFFICE
CERTIFICATE OF CORRECTION

PATENT NO. : 5,420,786

DATED : May 30, 1995

INVENTOR : MARK A. FELTHAUSER, ET AL.

It is certified that errors appear in the above-identified patent and that said Letters Patent is hereby corrected as shown below:

COLUMN 15

Line 66, "combing" should read --combining--.

COLUMN 17

Line 25, "Generating" should read --generating--.

COLUMN 18

Line 2, "locations;" should read --locations; and--.

Signed and Sealed this

Fifth Day of December, 1995

Attest:

BRUCE LEHMAN

Attesting Officer     Commissioner of Patents and Trademarks